United States Patent [19]
Dimeff

[11] 3,989,043
[45] Nov. 2, 1976

[54] AUTOMATIC FLOW CONTROL AND AUTOMATIC SHUT OFF FOR INTRAVENOUS FEEDERS

[76] Inventor: John Dimeff, 5346 Greenside Drive, San Jose, Calif. 95127

[22] Filed: Dec. 23, 1974

[21] Appl. No.: 535,390

[52] U.S. Cl. .................... 128/214 C; 128/214.2; 137/423; 137/430; 222/68
[51] Int. Cl.² .................................... A61M 5/16
[58] Field of Search ........ 128/214 R, 214 C, 214 E, 128/214.2, 227, 213; 222/67, 68; 137/390, 423, 430

[56] References Cited
UNITED STATES PATENTS

| | | | |
|---|---|---|---|
| 2,090,273 | 8/1937 | Wagner | 137/390 |
| 2,844,147 | 7/1958 | Beacham | 128/214 C |
| 3,092,106 | 6/1963 | Butler | 128/214 C |
| 3,543,752 | 12/1970 | Hesse et al. | 128/214 E |
| 3,584,764 | 6/1971 | Elkins | 222/67 |
| 3,756,233 | 9/1973 | Goldowsky | 128/214 C |
| 3,929,157 | 12/1975 | Serur | 128/214 C X |
| 3,931,818 | 1/1976 | Goldowsky | 128/214 C |

OTHER PUBLICATIONS
Lancet — Apr. 6, 1963, pp. 754–755.

*Primary Examiner*—Dalton L. Truluck
*Attorney, Agent, or Firm*—Darrell G. Brekke; Gary F. Grafel; John R. Manning

[57] ABSTRACT

An apparatus is disclosed for regulating the flow of solution from a fluid reservoir to the vein of a patient. All of the embodiments of the present invention include a first fluid chamber having an inlet and a discharge port and means disposed within a first fluid chamber for maintaining the level of solution therein between upper and lower levels. In all of the embodiments of the present invention, an upper and lower valve seat is provided within the first chamber which interacts with a float or floats contained therein to from two valve mechanisms which maintain a constant rate of flow of solution independent of the initial height or variations in height of solution contained within the reservoir during its depletion. In two of the embodiments of the present invention, a second fluid chamber is coupled to the first fluid chamber by means of a drip chamber which permits the visual counting of the rate of flow of solution from the first chamber to the second fluid chamber. The second fluid chamber is also provided with an intake and a discharge port that have valve seats disposed in close proximity thereto. A float is disposed within the second chamber for regulating the level of solution contained therein between an upper and a lower level. The float in combination with the valve seats forms upper and lower valve mechanisms which prevent the intake or discharge of solution from the second fluid chamber when the level of solution contained therein respectively reaches the upper and lower levels and maintains the rate of flow of solution through the second fluid chamber at the same rate maintained through the first fluid chamber. Additionally, the second fluid chamber regulates the flow rate of solution at all times within a rate of flow which may be safely tolerated by the patient.

6 Claims, 5 Drawing Figures

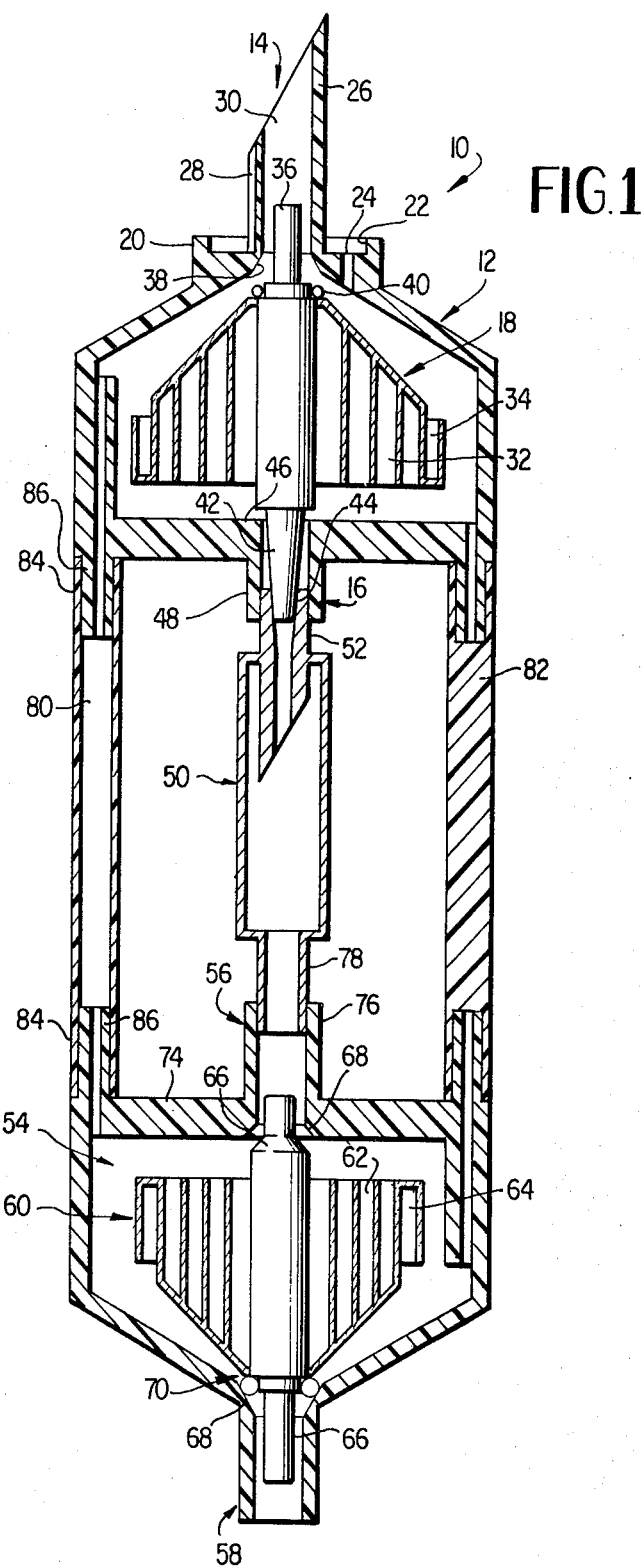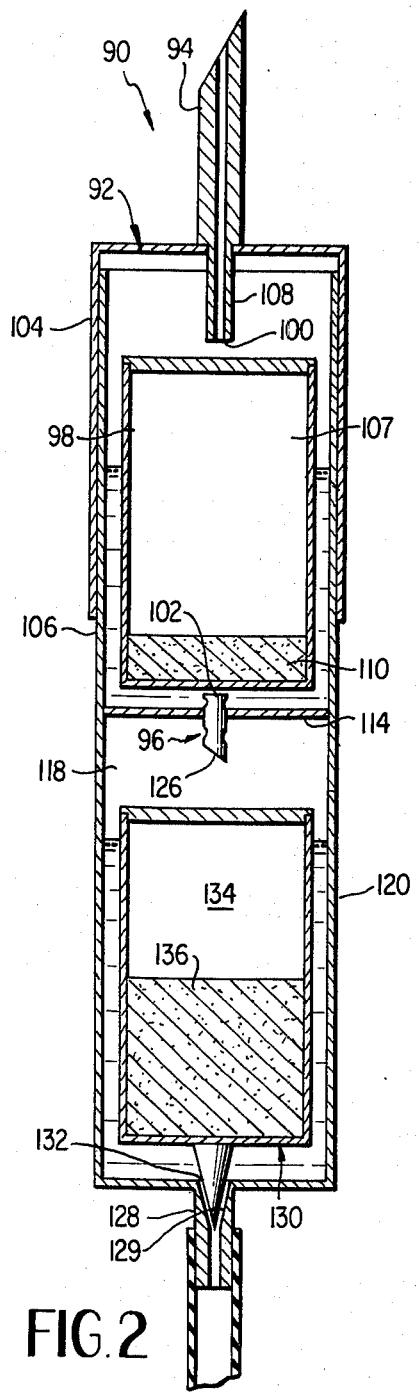
FIG.1
FIG.2

AUTOMATIC FLOW CONTROL AND AUTOMATIC SHUT OFF FOR INTRAVENOUS FEEDERS

DERIVATION OF THE INVENTION

The invention described herein is made by an employee of the United States Government and may be manufactured and used by or for the government for governmental purposes without the payment of any royalties thereon or therefor.

BACKGROUND OF THE INVENTION

1. Field of the Invention

The invention relates generally to apparatus for regulating the flow of solution from a reservoir into the vein of a patient and more particularly to solution flow regulating apparatus of the type which automatically maintains a constant rate of flow of solution into the vein of the patient and also shuts off the flow of solution into the patient's vein when the solution reservoir becomes empty to prevent the introduction of air.

2. Description of the Prior Art

U.S. Pat. No. 3,105,551, issued to Murphy, discloses an infusion safety valve which prevents the introduction of air into the patient's veins by means of an intravenous solution administering appartus. Murphy's invention comprises a bipartite chamber having inlet and discharge ports which are respectively adapted to be coupled to a solution reservoir and to the vein of the patient to whom the solution is being administered. The two chambers consist of an upper and a lower chamber. The lower chamber contains a float which has a piece of magnetic material mounted on its bottom. A piece of ferromagnetic material is mounted on the outside bottom surface of the lower chamber. When the solution contained within the lower chamber reaches a lower level, magnetic attraction between the float and the bottom of the chamber seats the float on the discharge port to prevent discharge of solution. Murphy, unlike the present invention, does not include any means contained within the fluid chamber for maintaining the flow of solution through the chamber at a constant rate independent of its initial height or variations in height of the solution level contained within the reservoir during depletion thereof. Additionally, Murphy's float does not regulate the upper level of solution which may be contained within the fluid chamber.

U.S. Pat. No. 2,844,147 issued to Beacham, U.S. Pat. No. 3,216,419, issued to Scislowicz, and U.S. Pat. No. 3,656,505 issued to O'Brian, each disclose an apparatus disposed within a drip chamber which is part of an intravenous feeding apparatus that prevents the introduction of air into the vein of the patient. Each of these devices utilizes a float-type device which functions as a valve to prevent the discharge of solution from the drip chamber when the level of solution contained therein becomes sufficiently low so that there is a danger of air being introduced into the vein of the patient through the drip chamber. Each of these devices differs substantially from the present invention in that the respective floats do not maintain a constant rate of flow of solution through the drip chamber independent of its initial height or variations in height of the solution reservoir; nor do they maintain the level of solution in the drip chamber between a lower and an upper level.

SUMMARY OF THE INVENTION

The disadvantages and limitations of the prior art intravenous flow controlling apparatus are obviated by the present invention which provides an intravenous solution flow control apparatus which prevents the introduction of air into the vein of the patient by a drip chamber and maintains a constant rate of solution flow into the vein of the patient independent of its initial height or variations in height of the solution reservoir while the solution reservoir is being depleted.

The preferred embodiment of the present invention may be summarized as follows. A first fluid chamber is provided having inlet and discharge ports. Upper and lower valve seats are located in proximity to the inlet and discharge ports. A float is contained within the first fluid chamber. The float and valve seats regulate the level and maintain a constant rate of flow of solution through the first chamber independent of its initial height or variations in height of the solution reservoir coupled to the inlet port. The top part of the fluid chamber has a sharp tip projecting vertically upward which is adapted to be inserted into a rubber stopper contained within the fluid reservoir. Disposed around the sharp tip is an annular recess defined by a vertical wall projecting upward from the top surface of the first fluid chamber. An air vent is cut in the channel of the recess to couple the outside atmosphere with the inside of the first fluid chamber. A longitudinal slot is cut in the outside surface of the sharp tip between a point close to the tip and the bottom of the angular recess to permit coupling of the outside atmosphere with the fluid reservoir when the sharp tip is inserted into the rubber stopper. A conduit is cut in the sharp tip to permit coupling of the interior of the first fluid chamber with the solution reservoir when the sharp tip is inserted in the rubber stopper. A conical valve seat is cut in the interior of the first fluid chamber in proximity to the intake port. The top of the float has a projection extending vertically upward to guide vertical movement of the float axially within the conical intake valve seat. An O-ring is disposed on top of the float and around the vertical projection to produce a valve which functions to prevent the flow of solution into the first fluid chamber when the solution level contained therein is at its upper level. The float contains at least one air entrapping compartment and at least one fluid entrapping compartment. The bottom of the float has a conical projection extending downward therefrom. The downward projection forms a valve which communicates with a conical valve seat which is axially aligned therewith and which is located in proximity to the discharge port. The conical valve and valve seat maintain a rate of flow of solution through the first fluid chamber which is linearly variable between low and high levels as a function of the vertical position of the float with respect to the conical valve seat. A second fluid chamber having inlet and discharge ports is coupled to the first chamber. A float is contained in the second fluid chamber. An intake and a discharge valve seat are respectively located in proximity to the intake and discharge ports. The function of the second fluid chamber and associated apparatus is to control the rate of solution flow to the patient's vein between maximum and minimum levels and to maintain the same steady rate of flow of solution that is maintained in the first fluid chamber. The float has a vertical projection extending upward therefrom to form a guideway to keep the axis of this float parallel to the principal axis of the apparatus and particularly with the discharge port of the lower chamber. The bottom of the float has a projection extending downward which functions as a valve which cooperates with the discharge valve seat. The float contains at least one solution-entrapping compartment and at least one air-entrapping compartment to compensate for the variation in the buoyant force exerted by solutions of different density. A drip chamber having transparent walls is coupled between the discharge port of the first fluid chamber and the intake port of the second fluid chamber to permit counting of the rate of solution flow. The position of the drip chamber is vertically moveable with respect to the first and second fluid chambers to permit adjustment of the discharge flow impedance of the first chamber. Adjustment of the vertical position of the drip chamber is produced by moving upper and lower cylindrical projections associated with the drip chamber with respect to axial sleeves projecting from the first and second chambers, an air conduit is provided which couples the first and second fluid chambers.

While the invention has been summarized in terms of its preferred embodiment, it is to be understood that the present invention also embraces alternative embodiments which will be fully described in the detailed description of the invention.

BRIEF DESCRIPTION OF THE DRAWINGS

FIG. 1 is a sectional schematic of the preferred embodiment of the present invention;

FIG. 2 is a sectional schematic of an alternative embodiment of the present invention;

Referring to FIG. 1, there is shown an automatic flow control and automatic shut off for intravenous feeders 10 that is constructed according to the present invention. A first fluid chamber 12 is provided having an intake port 14 and a discharge port 16. Float 18 disposed within the first fluid chamber 12. The fluid chamber 12 has a circular wall 20 extending upward from its top surface which defines an annular recess 22 having a vent 24 cut through the bottom of recess 22 that couples the outside atmosphere with the interior of chamber 12. Projecting vertically upward from fluid chamber 12 is a sharp tip 26 having two channels respectively 28 and 30 cut therein. The first channel 28 extends from near the tip of projection 26 down into the annular recess 22 to couple the outside atmosphere with a solution reservoir. The second channel 30 is adapted to couple the solution reservoir with the interior of the first fluid chamber when the sharp tip 26 is inserted into a rubber stopper contained within the solution reservoir. The circular wall 20 has radial slots cut therein which are designed to admir air to the recessed portion as the unslotted sections of 20 limit the motion of the present invention as it is thrust into the rubber stopper of the solution reservoir. The annular recess 22 is adapted to hold a sterilized cotton washer filter. The float 18 contains at least one air-entrapping compartment 32 which makes float 18 highly buoyant when suspended in a solution contained within the fluid chamber 12. At least one fluid-entrapping compartment 34 is provided for entrapping solution as it passes from the intake port 14. Extending vertically upward from float 18 is projection 36. Conical intake valve seat 38 is provided in close proximity to intake port 14. O-ring 40 is disposed on top of float 18 and centered around projection 36 to form a valve which functions to prevent the intake of solution when the level of solution within the fluid chamber 12 reaches an upper level. Conical projection 42 extends vertically downward from float 18 to form a valve. Conical discharge valve seat 44 cooperates with valve 42 to prevent the discharge of solution from the first fluid chamber 12 when the level of solution within the first fluid chamber 12 is at a lower level. The primary functions of the float 18 and valve 38 are to maintain a constant fluid level within fluid chamber 12 independent of the initial height or variations of height in the solution contained within the solution reservoir during its depletion and to maintain the solution level contained in fluid chamber 12 between a lower and an upper level. Similarly, float 18 and valve seat 44 comprise a means disposed within the first fluid chamber 12 for maintaining a constant rate of flow of solution independent of its initial height or variations in height of the solution in the solution reservoir during its depletion. The bottom 46 of the fluid chamber 12 extends vertically downward to form a hollow cylindrical boss 48. A drip chamber 50 is provided which has an extended cylindrical section 52 of smaller cross sectional area which is fixedly engaged by boss 48. Section 52 of the drip chamber 50 may be either interference fit within boss 48 or it may be threadedly engaged therewith. Adjustment of the vertical position of drip chamber 50 with respect to valve 42 adjusts the flow impedance of discharge port 16. This adjustment acts as a control of the flow rate of solution passing through the first chamber, by control of fluid discharge impedance; the primary rate also being controlled by the solution level in fluid chamber 12. The flow impedance of discharge port 16 is designed to be higher than the flow impedance of intake port 14 to permit the filling of fluid chamber 12 with solution. Drip chamber 50 is provided with transparent walls which permit the visual inspection of the rate of flow of solution passing through fluid chamber 12. A second fluid chamber 54 is coupled to fluid chamber 12 through drip chamber 50. Chamber 54 has an intake port 56 and a discharge port 58. A float 60 is provided which contains at least one fluid entrapment compartment 62 and at least one air entrapment compartment 64. The overall density of the float 62 is just slightly less than the least dense solution which is to be administered. Projecting upward from float 60 is conical intake valve 66. Intake valve seat 68 functions in combination with valve 66 to limit the intake of solution into the second fluid chamber when the level contained therein reaches an upper level. Extending downward from the bottom of float 60 is projection 66. Conical discharge valve seat 68 is disposed in proximity to discharge port 58 of the fluid chamber 34. The lower valve mechanism which is comprised of valve seat 68 and float 60 may be either a pulsatile type as shown or a continuously variable type. The continuously variable type has a flow impedance which is high enough to limit the flow from the second fluid chamber to a minimum included within the range of the present invention when the second fluid chamber is empty and which is low enough to allow a maximum flow rate when the solution level is high, and is smoothly variable between these limits as a function of the vertical position of float 60 with respect to the conical valve seat 68. In the case where the rate of flow of valve 70 is continuously variable, valve 70 consists of a conical projection disposed in the same axial position as alignment projection 66. The function of the lower valve mechanism is to prevent the discharge of solution from the second fluid chamber when the solution level is below a lower level. The upper wall 74 of the second fluid chamber 54 extends vertically upward into cylindrical hollow boss 76. Drip chamber 50 extends downward into an extended cylindrical section 78 of smaller cross sectional area which fixedly engages the inside of boss 76. The fixed engagement of boss 76 with extended section 78 of drip chamber 50 may be by either a force fit or by threaded engagement. Extending between the first fluid chamber 12 and the second fluid chamber 54 is a conduit 80 which couples the air space in the second fluid chamber 54 with the air space in the first fluid chamber 12 and to the outside atmosphere. The corresponding section 82 provided on the other side of the invention is of solid rather than tubular construction and supplies structural strength but does not link the air spaces in the first and second fluid chambers. Wall 82, like drip chamber 50, is made of transparent material so that the solution drip rate in chamber 50 can be readily observed. The displacement of float 60 is designed to be almost as large as the displacement of the second fluid chamber 54. As a result of this design, any increase or decrease in the output flow from chamber 54 will cause only a momentary output flow rate above or below flow limits which may be safely sustained by a patient until the float limits the flow rate back within a safe rate.

Figure 3:
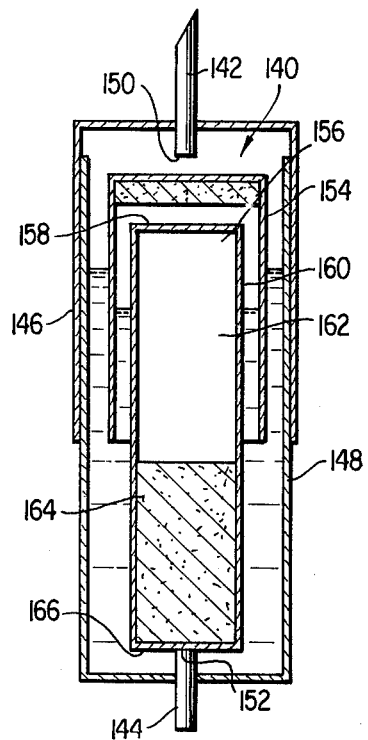
FIGS. 3–5 are further embodiments of the invention.

The preferred embodiment has a number of advantages which facilitate its use. The upper float control may be made in a single molding process. The external exposure of all of the surfaces of the upper float permit sterilization by exposure to appropriate gases. The fluid entrapment compartments provided in the upper and lower floats permit compensation for density variations in different solutions which may be administered to a patient. Venting of the first and second fluid containers with the outside atmosphere permits the invention to function independent of variations in air pressure. The venting of the first and second fluid chambers is by a common passageway which minimizes the space requirements of the apparatus. Venting of the air spaces above the first and second fluid chambers and the reservoir is through a common opening which does not require side ejection additions to the normal plastic mold used in fabrication. A pulsatile continuously active valve action regulating the discharge of fluid from the second chamber is possible. A transitory variation in the impedance of the output tube coupling the discharge port of the second fluid compartment with the patient's vein is possible without changing the steady state feed rate.

Referring to FIG. 2, there is shown an alternative embodiment 90 of the present invention. A first fluid chamber 92 is provided having an intake port 94 and a discharge port 96. Float 98, valve seats 100 and discharge port 102 are provided within chamber 92 to maintain a constant height of solution 6 in the chamber 106 which is independent of its initial height or variations in height of the solution in the source reservoir during its depletion and to regulate the fluid discharge rate from chamber 92. Chamber 92 is formed from a pair of telescoping containers 104 and 106. Containers 104 and 106 are axially moveable with respect to each other to permit varying of the upper level of solution within fluid chamber 92. Float 98 is designed to be substantially less dense that the least dense solution which will be introduced into fluid chamber 92. To produce this density, the float contains an entrapped air space 107 and a filler material 110. Discharge port 96 is constructed from a piece of perforated conduit to provide the desired solution flow through the first chamber at the fluid height determined by float 98 when it is pressed against input port 100. When the level of solution contained within fluid chamber 92 reaches its upper level, the top of float 98 seats against valve seat 100 to prevent further entry of solution. Float 98, upper valve seat 100 and lower discharge port 102 comprise a means disposed within the first fluid chamber for regulating the level of solution contained within the chamber and for maintaining a constant rate of flow of solution independent of the initial height or variations in height of the solution in the solution reservoir during its depletion. Partition 114 divides the first fluid chamber 92 from the second fluid chamber 120. A drip chamber 118 located within the second chamber 120 permits the counting of the rate of flow of solution through the first fluid chamber 92. The second fluid chamber 120 extends downward from partition 114. Tip 126 of discharge port 96 forms drops that are visible within the drip chamber 118. Valve seat 129 is located in the bottom of the fluid chamber 120. Float 130 is disposed within the second chamber 120. Conical valve seat 129 is located at the opening of discharge port 128. Float 130 is slightly less dense than the least dense solution which is to be administered by the present invention. This density is produced by having an air space 134 and a filler space 136 which contains a material which is more dense than the densest solution which is to be administered by the present invention.

Conical valve seat 129, float 130 and valve 132 comprise a means disposed within the second fluid chamber for regulating the level of the solution within the chamber 120 for maintaining the rate of flow of the solution at the same rate as the rate of flow of solution through the first fluid chamber 92 and for closing discharge port 128 if the fluid level in the second chamber 120 falls slightly because the incoming fluid flow through discharge port 96 is smaller than the discharge flow through 128.

Figure 4:
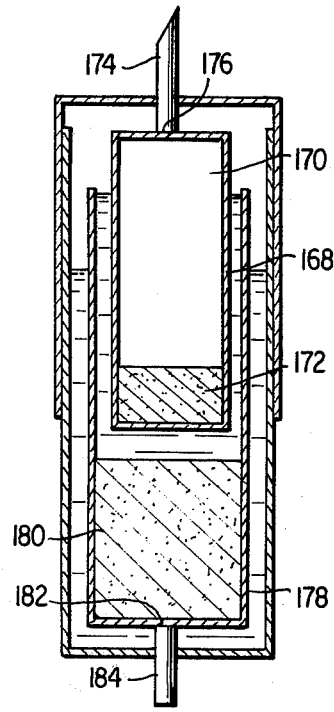

Referring to FIG. 3, there is shown a further embodiment of the present invention which may be described as follows. A first fluid chamber 140 is provided having an intake port 142 and a discharge port 144. Chamber 140 is constructed from two telescoping containers 146 and 148. To increase the solution which may be contained within the chamber 140, outer container 146 is slid upward with respect to container 148. Disposed in close proximity to intake port 142 and discharge port 144 are respectively intake valve seat 150 and discharge valve seat 152. Float 154 consists of a hollow cylindrical container closed at its upper end and open at lower end and so disposed within chamber 148 that it surrounds a second float 156. Intake valve seat 150 is located at the tip of intake port 142. Float 154 seats firmly on intake valve seat 142 to prevent the intake of solution into fluid chamber 140 when the level of solution reaches an upper limit. The second float 156 is disposed within the first float 154. Float 156 has a top 158, a body 160 which includes air chamber 162 and filler material 164. The density of the filler material 164 is chosen to impart an average density which is slightly less than the density of the least dense solution which is to be administered through the fluid chamber 140. The bottom of float 162 is disposed closest to lower valve seat 152 to form a valve which prevents theh discharge of solution from fluid chamber 140 when the level of solution falls to a lower level. Adjustment in the rate of flow of solution is produced by the displacement of telescoping container 146 with respect to 148 to vary the upper level of solution contained The embodiment illustrated in FIG. 4 is substantially the same as the one shown in FIG. 3. The difference resides in modifications made in the float structure. The remaining structure is identical to that described in conjunction with FIG. 3, and will not be discussed in detail. Float 168 is comprised of air chamber 170 and a filler material 172. The top of float 168 seats against valve seat 176 which is disposed on the end of the intake port 174. The overall density of float 168 is designed to be substantially less than the density of the least dense solution being fed into the fluid chamber 170. Float 168 functions to prevent the solution level from going above an upper level. The second float 178 consists of a container having a continuous closed wall which forms two openings; one opening being closed by filler material 180. The second float 168 fits inside the float 178 through the remaining opening. The filler material 180 in combination with solution contained therein and float 168 imparts on overall density to float 178 which is slightly less dense than the least dense solution which is to be administered through the fluid chamber. The bottom float 178 seats against a valve seat 182 which is disposed at the tip of the discharge port 184. The second float 178 prevents the level of solution from going below a lower level.

Figure 5:
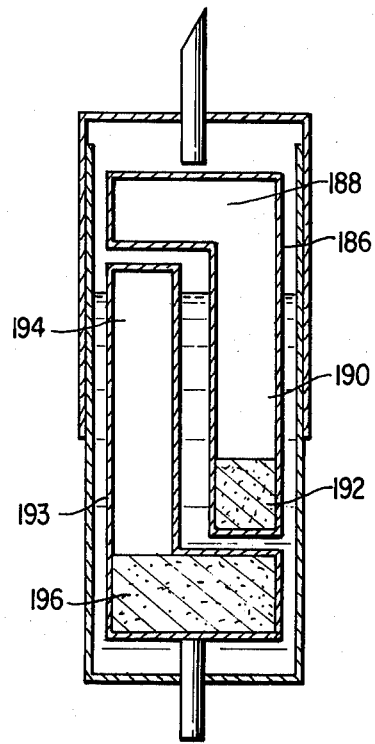

Referring to FIG. 5, discussion of the embodiment illustrated therein will be limited to the details of the float structure which differ from float structure of the preceeding two embodiments illustrated in FIGS. 3 and 4. Floats 186 and 192 have the same geometric configuration but are positioned within the fluid chamber with respect to each other with like geometric parts in an inverted orientation. Float 186, which regulates the upper level of solution contained within the fluid chamber, is comprised of two parts 188 and 190. The cross-sectional area of part 188 when viewed from a plane which is disposed perpendicular to the axis of the fluid chamber is larger than the cross-sectional area of the second section 190. All of the first section 188 and most of the second section 190 is filled with air. The bottom of section 190 has a filler material 192 which is used to impart increased density to float 186. The density of float 186 is designed to be substantially less than the least dense solution which is being administered through the fluid chamber. Section 188 is joined to section 190 so that the centroids of the aforementioned cross sections are offset with respect to each other. The density of float 192 is designed to be slightly less dense than the least dense solution that is administered through the first fluid chamber. The cross-sectional area of part 196 when viewed from a plane which is disposed perpendicular to the axis of the fluid chamber is larger than the cross sectional area of section 194. The first part 194 of float 193 is filled with air. The second part 196 of float 193 is substantially filled with a filler material. Section 194 is joined to section 196 so that the centroids of the aforementioned cross sections are offset with respect to each other.

Plastic is the preferred material from which all of the embodiments of the present invention are constructed. However, it should be apparent to those skilled in the art that other moldable materials may be used with equal facility.

OPERATION

The general mode of operation of the present invention is common to all of the embodiments described supra. Accordingly, if possible, the specific operation of all the embodiments of the present invention will be described in general terms which are generic to all of the embodiments. The upper float regulates the intake of solution into the first fluid chamber or in case of embodiments 3–5 into the fluid chamber. When the level of solution rises, this float rises in the chamber to the point where it seats against the intake valve seat of the chamber to prevent the introduction of additional solution. When the solution level drops, the upper float drops allowing introduction of additional solution. The upper float thus regulates the rate of discharge of solution from the reservoir supplying fluid to the first fluid chamber in such a way that the level of fluid in that first fluid chamber is constant and independent of the varying level of the fluid in the reservoir as the fluid supply in the reservoir is being depleted.

Each embodiment contains further a lower float arranged so as to activate a valve controlling the discharge of fluid from the lower reservoir and into the I-V tubing. When the solution level rises above the lower level, the float or the lower float rises to unseat the float from the discharge valve seat to permit discharge of solution. In the case of embodiments containing a tapered lower valve seat, or one otherwise arranged so as to allow gradual adjustment of the flow impedance, the lower float maintains a steady state discharge flow rate which is equal to the rate of solution flowing through the fluid chamber and determined by the controlled fluid height in the first chamber. In the case of embodiments containing a lower discharge valve designed to provide precipitous closure and opening, the lower valve operates in a "switched" mode, a drop of fluid entering the fluid chamber causes the lower float to rise slightly. The increased height of the fluid reduces the flow impedance of the lower exhaust port allowing the float to return to a stated position. Since the seated valve is fully closed, the fluid in the I-V tube acts to apply a downward pressure on the valve seat of the lower float, causing it to seat firmly and seal completely. The seal is maintained until entry of another drop of fluid falls into the chamber to reinitiate the cycle. In all embodiments, the flower valve seat is designed to provide full closure when flow from the supply reservoir is stopped by depletion of its supply or by its disconnection, during replacement of the supply, for example. The rate of flow of solution through the first fluid chamber or through the fluid chamber is determined by counting the rate of drop formation within the transparent drip chamber. In the case of the embodiments having a second fluid chamber, solution is introduced into the second fluid chamber via the intake port. The float and associated valves, which are similar to those used in the first fluid chamber, regulate the solution level between upper and lower levels and maintain a rate of steady state discharge from the second fluid chamber which is equal to the rate of flow of solution through the first fluid chamber. When the impedance of the line coupled between the discharge port of the second fluid chamber and the patient's vein either increases or decreases, the flow rate decreases or increases correspondingly until the float within the second chamber assumes a position or alternately closes and opens in a manner to limit the rate of solution flow within a range of flow rates sustainable by the patient. These limit flow rates are determined by the impedance of the intake and discharge ports of the second fluid chamber. To insure that the float is "fast" in regulating the flow rate from the second chamber to the patient's vein, the volume of the float is designed to displace almost all of the volume of the second fluid chamber.

While the invention has been described in terms of a preferred embodiment, and other embodiments, it should be understood that numerous modifications may be made to any of the embodiments which do not depart from the spirit and scope of the invention. Accordingly, it is intended that all such modifications fall within the scope of the appended claims.

What I claim as my Invention is:

1. An apparatus for regulating the rate of flow of solution from a fluid reservoir to the vein of a patient, the combination comprising:
   a. a first fluid chamber having intake and discharge ports, said intake being adapted to be connected to said fluid reservoir and said discharge port being adapted to be coupled to the vein of said patient;
   b. means disposed within said first fluid chamber for regulating the level of said solution contained within said chamber for regulating the level of said solution contained within said chamber between a lower and an upper level and for maintaining a constant rate of flow of solution independent of the initial height or variations in height of the solution in said fluid reservoir during its depletion;
   c. a second fluid chamber having an intake and a discharge port, said intake port being coupled to said discharge port of said first chamber, said discharge port of said second chamber being adapted to be coupled to the vein of said patient;
   d. means disposed within said second fluid chamber for regulating the level of solution contained within said second chamber between a lower and an upper level and for maintaining the steady state rate of flow of said solution from said second fluid chamber at the same rate as the rate of flow of solution from said first fluid chamber;
   e. said means disposed within said second fluid chamber for regulating the level of solution in said second fluid chamber comprising an upper and lower valve seat disposed in proximity to said intake and discharge ports, respectively, and a float disposed within said second fluid chamber, said float being vertically movable within said second fluid chamber upon application of buoyant force by said solution, said float seating against said upper valve seat to prevent the introduction of solution into said second fluid chamber from said first chamber when said solution level within said second fluid chamber is at the upper level and said float seating against said lever valve seat to prevent the discharge of solution from said second fluid chamber when the solution level within said second fluid chamber is at the lower level; and
   f. a drip chamber having transparent walls and disposed between the discharge port of said first fluid chamber and the intake port of said second chamber for forming drops of said solution to permit the counting of the rate of solution flow from said first chamber to said second fluid chamber.

2. In an apparatus for regulating the rate of flow of solution from a fluid reservoir to the vein of a patient as recited in claim 1 further comprising:
   a. said discharge valve seat of said second fluid chamber being conical in shape;
   b. a vertical projection extending downward from said float disposed in said second chamber to guide said float axially within said conical valve seat; and
   c. an O-ring disposed on said float and around said vertical projection which is adapted to form a seal with said conical valve seat.

3. In an apparatus for regulating the rate of flow of solution from a fluid reservoir to the vein of a patient as recited in claim 1 further comprising:
   a. said discharge valve seat of said second fluid chamber being conical; and
   b. a conical valve extending downward from said float, said valve having a linearly variable flow impedance between a low and high level which is a function of the vertical position of the float with respect to the second fluid chamber.

4. An apparatus for regulating the rate of flow of solution from a fluid reservoir to the vein of a patient, the combination comprising:
   a. a first chamber having intake and discharge ports, said intake port being adapted to be connected to said fluid reservoir and said discharge port being adapted to be coupled to the vein of said patient;
   b. means disposed within said fluid chamber for regulating the level of said solution contained within said chamber between a lower and an upper level and for maintaining a constant rate of flow of solution independent of the initial height or variations in height of the solution in said fluid reservoir during its depletion;
   c. a second fluid chamber having an intake and a discharge port, said intake port being coupled to said discharge port of said first chamber, and said discharge port of said second chamber being adapted to be coupled to the vein of said patient;
   d. means disposed within said second fluid chamber for regulating the level of solution contained within said second chamber between a lower and an upper level and for maintaining the steady state rate of flow of said solution from said second chamber container at the same rate of flow of solution from said first fluid chamber;
   e. said means disposed within said second fluid chamber for regulating the level of solution in said second fluid chamber comprising an upper and lower valve seat disposed in proximity to said intake and discharge ports, respectively, and a float disposed within said second fluid chamber, said float being vertically movable within said second fluid chamber upon application of buoyant force by said solution, said float seating against said upper valve seat to prevent the introduction of solution into said second fluid chamber from said first fluid chamber when said solution level within said second fluid chamber is at the upper level and said float seating against said lower valve seat to prevent the discharge of solution from said second fluid chamber when the solution level within said second fluid chamber is at the lower level;
   f. a vent hole cut in the top of said first fluid chamber to couple said first fluid container with the outside atmosphere;

g. a wall extending from said first fluid chamber to said second fluid chamber and surrounding said first fluid chamber discharge port and said second fluid chamber intake port, said wall having an air ductwork connecting the interior of said first fluid chamber with the interior of said second fluid chamber;

h. said fluid chamber having a wall with a sharp tip projecting upwardly which is adapted to be inserted into a rubber stopper located in the bottom of said fluid reservoir; said wall having an annular recess surrounding the base of said sharp tip;

i. an annular sterilizable air filter contained in said recess;

j. a conduit within said tip for coupling said fluid reservoir to the interior of said first fluid chamber; and k. an exterior slot extending from the upper end of said tip to said recess whereby the atmosphere can reach the interior of said fluid reservoir via said filter when said tip is inserted in said rubber stopper.

5. An apparatus for regulating the rate of flow of solution from a fluid reservoir to the vein of a patient, the combination comprising:

a. a first fluid chamber having intake and discharge ports, said intake port being adapted to be connected to said fluid reservoir and said discharge port being adapted to be coupled to the vein of said patient;

b. means including a float disposed within said first fluid chamber for regulating the level of said solution contained within said chamber between a lower and an upper level and for maintaining a constant rate of flow of solution independent of the initial height or variations in height of the solution in said fluid c. a second fluid chamber having an intake and a discharge port, said intake port being coupled to said discharge port of said first chamber, and said discharge port of said second chamber being adapted to be coupled to the vein of said patient;

d. means disposed within said second fluid chamber for regulating the level of solution contained within said second chamber between a lower and an upper level and for maintaining the steady state rate of flow of said solution from said second chamber at the same rate as the rate of flow of solution from said first fluid chamber;

e. means disposed within said second fluid chamber for regulating the level of solution in said second fluid chamber comprising an upper and lower valve seat disposed in proximity to said intake and discharge ports, respectively, and a float disposed within said second fluid chamber, said float being vertically movable within said second fluid chamber upon application of buoyant force by said solution, said float seating against said upper valve seat to prevent the introduction of solution into said second fluid chamber from said first fluid chamber when said solution level within said second fluid chamber is at the upper level and said float seating against said lower valve seat to prevent the discharge of solution from said second fluid chamber when the solution level within said second fluid chamber is at the lower level;

f. said float disposed in said first fluid chamber further comprising at least one liquid entrapping compartment and at least one separate air entrapping compartment, said liquid entrapping compartments each having an opening for accepting solution passing through the intake port of said first chamber to vary the density of said float disposed within said first chamber as a function of the density of said solution contained in said fluid reservoir; and g. said float disposed in said second fluid chamber further comprising at least one liquid entrapping compartment and at least one separate air entrapping compartment, said liquid entrapping compartments each having an opening for accepting solution passing through the intake port of said second chamber to vary the density of said float contained in said second fluid chamber.

6. An apparatus for regulating the rate of flow of solution from a fluid reservoir to the vein of a patient, the combination comprising:

a. a first fluid chamber having intake and discharge ports, said intake port being adapted to be connected to said fluid reservoir and said discharge port being adapted to be coupled to the vein of said patient;

b. means disposed within said first fluid chamber for regulating the level of said solution contained within said chamber between a lower and an upper level and for maintaining a constant rate of flow of solution independent of the initial height or variation in height of the solution in said fluid reservoir during its depletion;

c. a second fluid chamber having an intake and a discharge port, said intake port being coupled to said discharge port of said first chamber, and said discharge port of said second chamber being adapted to be coupled to the vein of said patient;

d. means disposed within said second fluid chamber for regulating the level of solution contained within said second chamber between a lower and an upper level and for maintaining the steady state rate of flow of said solution from said second chamber container at the same rate as the rate of flow of solution from said first fluid chamber;

e. said means disposed within said second fluid chamber for regulating the level of solution in said fluid chamber comprising an upper and lower valve seat disposed in proximity to said intake and discharge ports, respectively, and a float disposed within said second fluid chamber upon application of buoyant force by said solution, said float seating against said upper valve seat to prevent the introduction of solution into said second fluid chamber from said first fluid chamber when said solution level within said second fluid chamber is at the upper level and said float seating against said lower valve seat to prevent the discharge of solution from said second fluid chamber when the solution level within said second fluid chamber is at the lower level;

f. said intake valve seat of said first fluid container being conical;

g. a vertical projection extending upward from said float of said first fluid container to guide said float axially within said conical valve seat;

h. an O-ring disposed on said float of said first fluid container and around said vertical projection which is adapted to form a seal with said conical valve seat of said first fluid container;

i. a drip chamber having a top, a bottom, a transparent wall and disposed between the discharge port of said first fluid chamber and the intake port of said second chamber for forming drops of said solution to permit the counting of the rate of solution flow from said first chamber to said second chamber;

j. said discharge valve seat of said first fluid container being conical and connected to the top of said drip chamber;

k. a conical projection extending downward from said float of said first fluid container to form a valve which is movable with respect to said discharge valve seat of said first fluid chamber to produce a linearly variable flow impedance between low and high levels which is a function of the vertical position of said float within said first fluid chamber; and l. means for fixedly axially adjusting the position of the drip chamber with respect to said first and second fluid chamber to permit adjustment of the position of said lower conical valve seat of said first fluid chamber with respect to said conical projection extending from the float of said first fluid chamber to thereby adjust the flow impedance of said solution between said conical projection and said conical valve seat.

* * * * *